United States Patent [19]

Fredrickson

[11] Patent Number: 5,047,324

[45] Date of Patent: Sep. 10, 1991

[54] SUBSTANTIALLY PURE ENZYME-ANTIBODY CONJUGATE PREPARATIONS

[75] Inventor: Robert A. Fredrickson, Elkhart, Ind.

[73] Assignee: Miles Inc., Elkhart, Ind.

[21] Appl. No.: 95,621

[22] Filed: Sep. 16, 1987

Related U.S. Application Data

[63] Continuation-in-part of Ser. No. 939,640, Dec. 9, 1986, abandoned.

[51] Int. Cl.$^5$ .................. G01N 33/535; G01N 33/563
[52] U.S. Cl. ....................................... 435/7.9; 435/18; 435/188; 435/7.92; 436/512; 436/547; 530/388; 530/391
[58] Field of Search ................. 435/7, 18, 21, 25, 188, 435/810; 436/512, 518, 547; 530/391, 388

[56] References Cited

U.S. PATENT DOCUMENTS

| | | | |
|---|---|---|---|
| 4,551,426 | 11/1985 | Freytag et al. | 435/7 |
| 4,657,853 | 4/1987 | Freytag et al. | 435/7 |

OTHER PUBLICATIONS

Chambrach, *Methods of Protein Separation*, vol. 2, 1976, pp. 105–106.
Chambrach, *The Practice of Quantitative Gel Electrophoresis*, VCH, 1985, pp. 157–158.
Kraehenbuhl et al, *Journ. Cell Biol.*, 50, 432–445, 1971.
Avrameas, *Immunochemistry*, 6, 43–52, 1969.
Casu et al, *Ital. Journ. Biochem.* (Engl. Edn.), 18, 166–173, 1969.
Ram et al, *Journ. Cell Biol.* 17, 673–675, 1963.
Avrameas et al, *Immunochemistry*, 8, 1175–1179, 1971.
Davies et al, *Proc. Natl. Acad. Sci. U.S.A.* 66, 651–656, 1970.
Tijssen, *Practice and Theory of Enzyme Immunoassays*, Elsevier, Amsterdam, 1985, pp. 265–270.
Mashida et al, *Journal of Immunoassay*, 6, 111–123, 1985.
Imagawa et al, *Journal of Biochemistry*, 96, 1727–1735, 1984.
Kennedy et al, *Clinica Chimica Acta*, 70, 1–31, 1976.
Pillai et al, *Febs Letters*, 90, 51–53, 1978.

Primary Examiner—David A. Saunders
Attorney, Agent, or Firm—Andrew L. Klawitter; Daniel W. Collins

[57] ABSTRACT

A method for obtaining a substantially pure preparation of an enzyme-antibody conjugate having an enzyme component covalently coupled to a predetermined number of an antibody component where the molecular weight of the enzyme component is substantially greater than the molecular weight of the antibody component. The method involves the electrophoretic separation of the desired enzyme-antibody conjugate from an enzyme-antibody conjugate reaction mixture comprising, as separately migratable species, at least a free enzyme component and a population of enzyme-antibody conjugates comprising one or more of the enzyme component convalently coupled to one or more of the antibody component. The resulting conjugate preparations are substantially pure and are therefore particularly useful as labeled reagents in immunometric assays.

5 Claims, No Drawings

SUBSTANTIALLY PURE ENZYME-ANTIBODY CONJUGATE PREPARATIONS

CROSS-REFERENCE TO RELATED APPLICATION

This application is a continuation-in-part of U.S. patent application Ser. No. 939,640, filed Dec. 9, 1986, now abandoned.

BACKGROUND OF THE INVENTION

The present invention relates to labeled reagents which are useful as detection reagents in analytical test systems. In particular, the present invention relates to enzyme-labeled antibodies which are useful as labeled reagents in an immunoassay.

The development of various immunoassay test formats and systems for the detection of analyte in a liquid test sample has given rise to the use of labeled reagents, particularly enzyme-labeled antibodies, to monitor the extent of antigen-antibody binding in an immunoassay. Generally, such test formats and systems involve a labeled reagent comprising a labeled form of the analyte of interest or an antibody thereto, which is combined with a test sample containing the analyte of interest to form a binding reaction system producing two species of the labeled reagent, a bound species and a free species. The relative amount or proportion of the labeled reagent that results in the bound species compared to the free species is a function of the presence or amount of analyte in the test sample. Where the labeled reagent is a labeled form of an antibody, such immunoassay is referred to as an immunometric assay or, more particularly, where the label of such labeled antibody is an enzyme, an enzyme immunometric assay.

The first use of enzyme-labeled antibodies was described by Avrameas and Uriel [*Compt. Rend., Ser. D.*, Vol. 262, 2543-5(1966)] and Nakane and Pierce [*J. Histochem. Cytochem.*, Vol. 14, 929(1966)] for use in immunocytochemical detection. Enzyme-labeled antibodies have also been used in quantitative enzyme-linked immunoassays [Engvall and Perlmann, *Immunochemistry*, Vol. 8, 871(1971) and U.S. Pat. No. 3,654,090], and since that time, various procedures have been described for coupling antibodies, particularly monovalent fragments [Fab', i.e., containing sulfhydryl groups in the hinge region, or Fab, i.e., containing no hinge region sulfhydryl groups] thereof, to various enzymes to provide enzyme-antibody conjugates of varying stoichiometries. Although divalent antibody fragments [F(ab')$_2$] or IgG can be employed in such assays, monovalent antibody fragments (Fab') are preferred because of improved assay sensitivity. Such improved sensitivity of Fab' fragments over F(ab')$_2$ fragments or IgG is due to the indistinguishability of monosaturated divalent antibodies from unsaturated antibodies in terms of their binding behavior, whereas when monovalent antibodies are employed, there will be a one-to-one correspondence between binding of sample analyte and displacement of labeled antibody.

For example, Freytag, et al. [*Clin. Chem.*, Vol. 30, No. 3, 417-420 and Vol. 30, No. 11, 1809-1811(1984) and U.S. Pat. No. 4,434,236] describe methods for coupling Fab' monovalent antibody fragments to $\beta$-D-galactosidase. Similarly, Yoshitake et al. [*Eur. J. Biochem.*, Vol. 101, 395-399(1979)] describe methods for coupling Fab' fragments to glucose oxidase.

The known methods of conjugation involve random techniques of protein-protein conjugation which result in conjugates of varying stoichiometry, as well as contaminants such as free enzyme and free antibody components. Such contaminants, when present, significantly interfere with the sensitivity of an enzyme immunoassay. In particular, free enzyme in the conjugate mixture results in an increased background in an immunometric assay and, accordingly, decreased precision. Similarly, the presence of free antibody or fragments thereof in a conjugate preparation results in decreased assay sensitivity and nonlinear dose response in an immunometric assay. Moreover, in order to obtain high assay sensitivity and a linear dose response, it is preferred to employ monoconjugates (i.e., one enzyme component coupled to a single antibody component) rather than polyconjugates (i.e., enzyme component coupled to more than one of the antibody component) in an immunoassay.

Accordingly, a number of methods for conjugating enzymes and antibodies to achieve a monoconjugate and methods of purification in order to overcome the problems presented by the presence of enzyme and/or antibody contaminated conjugates have been attempted. However, the preparation of a substantially pure enzyme-antibody monoconjugate has been successful only with enzymes having a comparable molecular weight to the antibody component. For example, Ishikawa, et al. [*J. of Applied Biochemistry*, Vol. 4, 41 (1982) and *J. Biochem.*, Vol. 92, 1413(1982)] describe horseradish peroxidase (activated with succinimidyl-4-(N-maleimido-methyl)cyclohexane-1-carboxylate) coupled to Fab' fragments where the monoconjugate thereof was isolated by gel filtration and immunopurified [*Analytical Letters*, , Vol. 17, 229 and 2076(1984)].

Although gel filtration and immunopurification have been shown to be successful for isolating Fab'-horseradish peroxidase monoconjugates as heretofore described, such methods are inadequate to separate and isolate monoconjugates of Fab' fragments and enzymes of disparate molecular weights, such as Fab'-glucose oxidase [*Eur. J. Biochem.*, Vol. 101, 395(1979)], Fab'-alkaline phosphatase [*Scand. J. Immunol.*, pk Vol. 8, 43-55(1980)], and Fab'-$\beta$-D-galactosidase [*Analytical Letters*, Vol. 18(1311), 1331-1334(1985)]. Such methods are not only inadequate to separate monoconjugates from polyconjugates, as well as from free enzyme components, immunopurification often results in low conjugate recovery and risk of enzyme and/or antibody inactivation.

There is also described in *FEBS Letters*, Vol. 90, 51(1978), a gel filtration-elution method to isolate IgG-invertase monoconjugate by immobilizing invertase to a Con A column, activating the immobilized invertase, and then adding IgG to the column. The resulting conjugate was then desorbed from the affinity support and purified by gel filtration. However, the method produced conjugates having protein:enzyme and antibody binding site:enzyme ratios of 1:1 and 2:1, respectively, and, accordingly, did not yield a monoconjugate, i.e., comprising 1:1 proportions for both protein:enzyme and antibody binding site:enzyme ratios. In addition, such method resulted in a major portion of unconjugated IgG, i.e., low levels of conjugation, and further, the gel filtration step would be effective to isolate a monoconjugate only if the two proteins were comparable in molecular weight as previously discussed.

The difficulty of separating and isolating monoconjugates of antibodies and enzymes of disparate molecular weights to obtain a pure preparation thereof has also been illustrated [*BioChromatography*, Vol. 1, 42(1986)] employing the most advanced HPGFC (high performance gel-filtration chromatography) techniques, particularly IgG conjugates of horseradish peroxidase, alkaline phosphatase, and β-D-galactosidase. In particular, an IgG-β-D-galactosidase conjugate mixture was purified on a gel filtration column (Sepharose ® CL-4B) to obtain a fraction consisting predominantly of free β-D-galactosidase, and other large molecular weight aggregates. This pooled fraction was loaded to the HPGFC column and three peaks without baseline resolution were observed in the chromatogram. The predominant peak was unreacted β-D-galactosidase; another peak which eluted first in the chromatogram was presumably aggregated conjugate. The small peak which eluted between these two was alleged to be monoconjugate (1:1 IgG-β-D-galactosidase) although no evidence was offered. Undoubtedly this fraction contained some monoconjugate but was probably contaminated with both free enzyme and polyconjugates. Given this general lack of resolution in this molecular weight range, the likelihood of resolving a 1:1 Fab-β-D-galactosidase conjugate would be very small using this technique.

Accordingly, it is an object of the present invention to provide a method for separating and isolating enzyme-antibody monoconjugates and polyconjugates comprising enzyme and antibody components of disparate molecular weights from each other and from contaminating free enzyme components and free antibody components.

Another object of the present invention is to permit the use of enzyme and antibody stoichiometries which drive the coupling reaction of enzyme and antibody to maximum conjugate production at high, preparative yields.

Further, it is an object of the present invention to provide a highly sensitive and precise immunometric assay having little or no background signal.

Still further, it is an object of the present invention to provide an enzyme-antibody conjugate having maximum enzyme and antibody activity.

SUMMARY OF THE INVENTION

The present invention provides a method for producing a substantially pure preparation of an enzyme-antibody conjugate comprising an enzyme component covalently coupled to a predetermined number of an antibody component where the enzyme component has a molecular weight which is at least about 1-fold greater (i.e., 100% or 2 times greater) than the molecular weight of the antibody component, preferably between about 2- and about 20-fold greater. The method comprises the steps of (a) applying an enzyme-antibody conjugate reaction mixture to an electrically neutral, solid, porous, electrophoretic support matrix, the conjugate reaction mixture comprising, as separately migratable species, at least a free enzyme component and a population of enzyme-antibody conjugates comprising one or more of the enzyme component covalently coupled to one or more of the antibody component, (b) electrophoretically separating the enzyme-antibody conjugates into distinct concentration zones on the support matrix, and (c) isolating a substantially pure preparation of the desired enzyme-antibody conjugate from one or more of the respective concentration zones. The resulting substantially pure enzyme-antibody conjugate preparations which can be isolated from their respective concentration zones include both monoconjugates having one enzyme component covalently coupled to one antibody component and polyconjugates having one enzyme component covalently coupled to more than one of an antibody component (e.g., diconjugates, triconjugates, etc.). Such preparations comprise, individually, greater than about 90%, usually greater than 95%, more usually greater than 99%, of the enzyme component present in the isolated preparation covalently coupled to the predetermined number of the antibody component.

Accordingly, the disadvantages of the enzyme-antibody conjugate purification techniques heretofore described are overcome by the method of the present invention which separates substantially all of the enzyme-antibody conjugates from free enzyme and antibody components of disparate molecular weights present in an enzyme-antibody conjugate reaction mixture without the need for an affinity step. The present method therefore provides enzyme-antibody conjugates having maximum enzyme and antibody activity, and permits the use of enzyme and antibody reaction stoichiometries which result in maximum conjugate production of high, preparative yields.

DESCRIPTION OF THE PREFERRED EMBODIMENTS

The enzyme-antibody conjugates of the substantially pure conjugate preparations of the present invention comprise covalently coupled enzyme and antibody components and are characterized by the enzyme component having a molecular weight which is substantially greater than the molecular weight of the antibody component, usually at least about 1-fold greater, more usually from between about 2-fold and about 20-fold greater, and preferably from between about 2.5-fold and about 10-fold greater.

It is to be appreciated that, generally, it is desirable to employ purified homogeneous enzyme-antibody conjugates in an immunoassay, i.e., free from enzyme and antibody contamination, because known stoichiometry permits the assignment or determination of an extinction coefficient, e.g., for spectral measurements and protein quantification, the accurate assessment of the specific activities for both the antibody and enzyme components of the conjugate, and the determination of the number of analyte binding sites for each active enzyme center. More preferably, the use of an enzyme-antibody monoconjugate, i.e., one antibody component for each enzyme component, in an immunoassay maximizes high sensitivity and precision of such immunoassay.

Accordingly, the method of the present invention fulfills such criteria by providing a substantially pure preparation of a desired enzyme-antibody conjugate, substantially free from enzyme and antibody contamination, wherein greater than about 90%, usually greater than about 95%, more usually greater than about 99%, of the enzyme component present in the isolated preparation is covalently coupled to the desired number of the antibody component.

Antibody Component

The antibody component of the enzyme-antibody conjugates of the present invention can be a whole antibody, such as any of the classes and subclasses of known immunoglobulins, e.g., IgG, IgM, and the like, or monovalent and divalent antibody fragments of IgG, conventionally known as Fab and Fab', and F(ab')$_2$, respectively. The immunoglobulin source for the antibody component can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglubulins can also be obtained by somatic cell hybridization techniques, such resulting in what are commonly referred to as monoclonal antibodies, also involving the use of an appropriate immunogen.

The antibody component will commonly be a whole IgG antibody, preferably a divalent antibody fragment [F(ab')$_2$], more preferably a monovalent antibody fragment (Fab or Fab') thereof. The molecular weight of the divalent IgG fragment is approximately 100,000 daltons, and the molecular weight of the monovalent IgG fragments is approximately 50,000 daltons.

Divalent and monovalent IgG antibody fragments can be obtained according to methods known in the art employing standard proteolytic digestion procedures with pepsin or papain. For example, divalent antibody fragments [F(ab')$_2$] can be prepared by digesting the whole IgG antibody with pepsin [Nisonoff, *Methods Med. Res.*, Vol. 10, 132(1964)], and then reducing the F(ab')$_2$ fragment to the corresponding Fab' fragment with dithiothreitol. Alternatively, Fab fragments can be obtained by papain digestion of IgG [Porter, *Biochem. J.*, Vol. 73, 119(1959)].

According to the present invention, the antibody component is preferably a monovalent Fab' fragment. Preferably, ascites fluid containing the desired whole IgG antibody is first treated with pepsin to obtain the F(ab')$_2$ divalent antibody fragments, and then purified on an immunoaffinity column according to methods known in the art. Alternatively, F(ab')$_2$ fragments can be prepared by first isolating whole IgG from ascites fluid on a protein A column, treating the isolated IgG with pepsin, and then purifying the resulting F(ab')$_2$ fragments by immuno-affinity, protein A or gel filtration chromatography according to methods known in the art.

The Fab' monovalent antibody fragment is then prepared by reducing the F(ab')$_2$ divalent antibody fragment with reducing agents such as $\beta$-mercaptoethanol, cysteine, dithiothreitol, or mercaptoethylamine, and the like. The number of available sulfhydryl groups of the Fab' fragment are determined according to methods known in the art employing 4,4'-dithiopyridine [Grassetti and Murray, Jr., *Arch. Biochem. Biophys.* 119, 41(1967)]. The sulfhydryl groups in the hinge region (1-4 sulfhydryls), remote from the antigen binding site, are preferable sites for coupling the Fab' antibody component to the enzyme component, as will be described in greater detail hereinafter.

Enzyme Component

According to the present invention, the enzyme component can be selected from a wide variety of enzymes having a molecular weight of at least about 1-fold greater than the molecular weight of the antibody component to which it is coupled, usually from between about 2- and about 20-fold greater, preferably from between about 2.5- and about 10-fold greater, and which can be coupled to an antibody component. It should be recognized that an important feature of the method of the present invention is the ability to achieve the separation of enzyme-antibody monoconjugates and polyconjugates, into separate and distinct zones thereof, from free enzyme and antibody components, even where there is substantial disparity in molecular weight between the enzyme component and the antibody component thereof. Accordingly, such disparity, of course, will depend upon the relative molecular weights of the enzyme selected as the enzyme component and the particular antibody component selected, i.e., whole IgG (150,000 daltons), F(ab')$_2$ (100,000 daltons), Fab' (50,000 daltons).

Particular enzymes that can be used include, but are not intended to be limited to, $\beta$-D-galactosidase (465,000 daltons), glucose oxidase (150,000 daltons), alkaline phosphatase (125,000 daltons), glucose-6-phosphate dehydrogenase (104,000 daltons), luciferase (80,000 daltons), pyruvate kinase (237,000 daltons), lactate dehydrogenase (137,000 daltons), galactose oxidase (68,000 daltons), tyrosinase (128,000 daltons), invertase (320,000 daltons), xanthanine oxidase (275,000 daltons), urease (540,000 daltons), uricase (100,000 daltons), alcohol oxidase (630,000 daltons) and the like.

$\beta$-D-galactosidase, which is purified from the bacterium *Escherichia coli* and commercially available (Sigma Chemical Co., St. Louis, Mo., USA), is particularly preferred because it possesses a very high enzymatic (i.e., substrate) turnover number and a low dissociation constant ($K_m$) for the enzyme-substrate complex, is relatively stable to permit extended periods of storage with little or no loss in enzymatic activity, exhibits little or no interference from biological fluids, and possesses many reactive surface sulfhydryl groups which can be derivatized with little or no loss in enzymatic activity. However, because of its relatively large molecular weight, i.e., 465,000 daltons, prior to the method of the present invention, attempts to obtain an enzyme-antibody monoconjugate employing $\beta$-D-galactosidase as the enzyme component have been particularly unsuccessful.

It is to be understood that the enzyme component of the enzyme-antibody conjugate can be a single enzyme molecule to which one or more of the antibody component is coupled, or can be a complex of two or more enzyme molecules to which one or more of the antibody component is coupled. For example, two or more enzymes can be crosslinked to form a polymerized enzyme component, such as described by European Pat. Application No. 175,560, and one or more of the antibody component coupled thereto. Similarly, aggregated enzyme-antibody conjugates can be prepared employing glutaraldehyde crosslinking [Avrameus, S., *Immunochemistry*, Vol. 6, 43 (1969)], periodate oxidation and other crosslinking agents known in the art.

Enzyme-Antibody Coupling Techniques

Various methods for coupling enzymes to antibodies are known in the art [see, for example, *Methods in Enzymology*, van Vunakis and Langone (eds.), Vol. 70(1980) and Vol. 73(1981)] employing various crosslinking reagents. Such reagents include homobifunctional and heterobifunctional crosslinking reagents, the latter being preferred. Homobifunctional crosslinking reagents include dimethyl suberimidate 2HCl, dimethyl pimelimidate, 3,3'-dithiobis(sulfosuccinimidyl propionate), bis(sulfosuccinimidyl)suberate, o-phenylenedimaleimide, bis(maleimido)methyl ester, dimethyl adipimidate, dithiobis(succinimidyl propionate), and the like. Heterobifunctional crosslinking reagents include m-maleimidobenzoyl sulfosuccinimide ester, N-succinimidyl 3-(2-pyridyldithio)propionate, succinimidyl4-(N-maleimidomethyl)cyclohexane-1-carboxylate, sulfosuccinimidyl6-(4'-azido-2'-nitrophenylamino)-hexanoate, succinimidyl-4-(p-maleimidophenyl)butyrate, N-5-azido-2-nitrobenzoyloxysuccinimide, N-succinimidyl(4-iodoacetyl)aminobenzoate, maleimidohexanoyl-N-hydroxysuccinimide ester, m-maleimidobenzoyl-N-hydroxysuccinimide ester, sulfoxuccinimidyl-4-(N-maleimidomethyl)cyclohexane-1-carboxylate, sulfosuccinimidyl-4-(p-maleimidophenyl)-butyrate, N-hydroxysuccinimidyl-4-azidobenzoate, and the like.

Generally, such crosslinking reagents are reacted with an appropriate antibody component to generate an activated antibody component which can then be reacted with the selected enzyme to produce the desired enzyme-antibody conjugate. For example, Fab or F(ab')$_2$ antibody fragments can be treated with a crosslinking reagent such as succinimidyl-4-(N-maleimidomethyl)cyclohexane-1-carboxylate [SMCC] to generate Fab or F(ab')$_2$-maleimido-activated antibody fragments. The maleimido-activated antibody fragments can then be reacted with the selected enzyme to produce the desired enzyme-Fab or -F(ab')$_2$ conjugate.

More particularly, where the desired enzyme component is $\beta$-D-galactosidase and the desired antibody component is Fab', the coupling thereof is preferably achieved by first blocking the surface-exposed sulfhydryl groups of $\beta$-D-galactosidase with an alkylating reagent, such as iodoacetamide, and then reacting the alkylated $\beta$-D-galactosidase with SMCC as the crosslinking reagent to incorporate reactive maleimide groups into the enzyme. Accordingly, when the maleimide-activated $\beta$-D-galactosidase is reacted with the Fab' antibody fragment, the sulfhydryl groups of the Fab' fragment react with the $\beta$-D-galactosidase-maleimide groups to form a covalent bond therebetween.

It is to be appreciated that according to methods known in the art as heretofore described for the preparation of enzyme-antibody conjugates, a conjugate reaction mixture comprising enzyme-antibody monoconjugates and polyconjugates, and one or more contaminants such as unreacted enzyme and antibody components, will be formed. Accordingly, since it is desirable to employ substantially homogeneous reagents in an immunoassay as heretofore described, particularly a substantially pure preparation of an enzyme-antibody monoconjugate or polyconjugate, it is necessary to separate the desired enzyme-antibody conjugates from any of such contaminants in the conjugate reaction mixture.

Purification of Monoconjugate and Polyconjugates

According to the present invention, the enzyme-antibody conjugates are separated from free enzyme and free antibody components present in an enzyme-antibody conjugate reaction mixture on an electrically neutral, solid, porous, electrophoretic support matrix. Once separated, one or more of a desired enzyme-antibody conjugate can be isolated from the support matrix into substantially pure preparations thereof.

Generally, electrophoresis is a method whereby charged molecules migrate through a medium in response to an electric field as a function of their charge, shape, size and the temperature of the particular medium. In particular, macromolecules such as proteins, i.e., enzymes and antibodies, are composed of a series of amino acids which individually are acidic, basic or neutral, depending on the pH of the medium and, accordingly, such amphoteric nature thereof results in an overall net charge which can be positive, negative, or zero, respectively. The isoelectric point (pI) of a protein is the pH at which the net charge of the protein is zero. At a pH below the pI, the protein is positively charged; above the pI, negatively charged. The extent of deviation of the pH from the pI is directly proportional to the net charge of the protein.

Accordingly, electrophoresis has been found to be particularly useful in separating an enzyme-antibody conjugate comprising enzyme and antibody components of disparate molecular weights as heretofore described. The electrophoretic support matrix is generally a porous material such as agarose, polyacrylamide gel, starch gel, paper, cellulose acetate, and the like, preferably polyacrylamide. Such support matrix inhibits convections caused by heating and can be stained to provide a record of the electrophoretic process which permits scanning, autoradiography, and other analytical techniques. Porous support gel matrices such as agarose and polyacrylamide are especially useful because of the ability of such matrices to separate molecules on the basis of their physical differences both in molecular size or weight and net charge. In particular, when there are only a few components to be separated, i.e., free enzyme and antibody components and enzyme-antibody monoconjugates and polyconjugates, an exact determination of the optimum pore size of the gel for separating the enzyme-antibody conjugates from the free enzyme and antibody components as separately migratable species is possible.

Generally, gels such as polyacrylamide and agarose can be prepared with restrictive porosities which act as sieves to retard or obstruct the movement of macromolecules while, at the same time, permit the free movement of smaller molecules therethrough. Where agarose is employed as the porous gel matrix, the pore size can be predetermined by adjusting the concentration of agarose in the gel so that the higher the concentration of agarose employed, the smaller the pore size will be. Generally, working concentrations of agarose in a gel thereof is from between about 0.4 and about 2.0% w/v.

In the case of polyacrylamide, which is particularly preferred according to the present invention and known in the art as polyacrylamide gel electrophoresis (PAGE), it is to be understood that in forming a polyacrylamide gel, the acrylamide monomers polymerize into long copolymer chains that are covalently linked by a crosslinker, such as N,N'-methylenebisacrylamide. The polymerization of a polyacrylamide gel is generally accomplished employing an initiator, such as ammonium persulfate, and a catalyst, such as N,N,N',N'-tetramethylethylenediamine (TEMED). Accordingly, the pore size of a polyacrylamide gel can be predetermined by adjusting the total percentage of acrylamide, e.g., the sum of the weights of the acrylamide monomer and the crosslinker, expressed as % T. For example, a 20% T gel would contain 20% w/v of acrylamide plus the crosslinker, wherein as the % T increases, the pore size decreases. Similarly, the pore size can be adjusted by varying the amount of crosslinker, expressed as a percent of the sum of the monomer and crosslinker (% C). For example, a 20% T-5% C gel would have 20% w/v of acrylamide plus the crosslinker, and the crosslinker would account for 5% of the total weight of the acrylamide.

The sieving effect of the gels and the different net charges of the macromolecules to be separated result in the separation of the macromolecules into concentration zones or band regions on the gel which can then be physically removed to isolate the particular separately migratable species contained therein, as will be described in greater detail hereinafter.

For example, where the enzyme component of the enzyme-antibody conjugate reaction mixture is $\beta$-D-galactosidase (pI=4.5), at any pH above 4.5, it is negatively charged and will migrate under the influence of an electric field toward the positive electrode. It is to be understood that the antibody component, e.g., Fab', is a minor perturbation to the pI of the enzyme when conjugated because of its relatively small size. Its pI of 7.5–8.0 causes the pI of the monoconjugate to be slightly greater than the pI of the enzyme alone. Accordingly, where a monoconjugate is desired, the free enzyme component would migrate faster toward the positive electrode than the enzyme-antibody monoconjugate at a pH above both their respective pI's under the influence of an electric field. Analagously, in the case of polyconjugates, e.g., diconjugates and triconjugates comprising two or three antibody components, respectively, coupled to an enzyme component, the diconjugate would migrate slower than the monoconjugate and the triconjugate would be still slower. The antibody fragments, although relatively small, generally migrate even slower than the above-mentioned compounds because of their relatively high pI. As will be described in greater detail hereinafter, the nature of contaminants present in an enzyme-antibody preparation, such as free enzyme and antibody components and undesired enzyme-antibody conjugates, will depend upon the proximity of the desired enzyme-antibody conjugate relative to such contaminants on the electrophoretic support matrix.

(i) Preparation of PAGE Apparatus

According to the present invention, the use of a PAGE apparatus to separate and isolate a substantially pure enzyme-antibody conjugate preparation is particularly preferred. The PAGE apparatus consists of two electrophoretic components comprising a vertical slab polyacrylamide gel and an electroelution device for isolating the desired migratable species of a band region which is removed from the gel after the desired separation has occurred. The vertical slab gel is poured with both a polyacrylamide and a density gradient. The polyacrylamide gradient increases from the top to the bottom of the gel. In principle, this should result in band focusing and narrow band widths because the particular protein's rate of migrataion becomes progressively slower as it migrates down the gel until it eventually stops due to being blocked by the small pore size of the gel. This mechanism helps to reverse the band-broadening trends such as sample loading and diffusion, which are always operative during a PAGE run.

The density gradient facilitates the effective pouring of the polyacrylamide gradient by preventing convection currents. The gradients are poured by connecting two solutions in series, such as, for example, a first container containing a solution of 10% acrylamide and 15% sucrose, and a second container containing a solution of 5.0% acrylamide. The solution of the first container is first permitted to flow into a vertical slab sandwich comprising two glass plates spaced approximately 6 mm apart while, at the same time, the solution of the second container is permitted to flow into the first container to mix with the solution therein. Accordingly, the first liquid to flow into the glass sandwich is both high in polyacrylamide monomer (initially 10%) and physical density (15% sucrose), and the subsequent flowing liquid will always be lower in polyacrylamide monomer and in density (sucrose). Since the density of the incoming flow is always lower, it does not agitate the liquid which is already in the glass sandwich and the polyacrylamide is therefore maintained uniformly from top to bottom in a linearly increasing concentration gradient.

It is to be understood that the total percentage of acrylamide and amount of the crosslinker will depend on the desired pore size necessary to separate the various enzyme-antibody conjugates present in the reaction mixture as heretofore described, which will depend, of course, upon the size and overall charge of the particular enzyme and antibody components employed. Accordingly, such adjustments can be made by one skilled in the art apprised of such considerations in order to provide a suitable polyacrylamide gel for the purification of an enzyme-antibody conjugate according to the present invention.

(ii) Operation of the PAGE Apparatus

According to the present invention, an enzyme-antibody conjugate reaction mixture is applied to the top of the vertical slab polyacrylamide gel, such as into a sample well formed at the top of the gel according to methods known in the art. The conjugate reaction mixture is then electrophoresed at a constant voltage of, for example, 100 volts, to separate, as separately migratable species, substantially all of the enzyme-antibody conjugates into their respective concentration zones or bands in the polyacrylamide gel, which are separate and distinct from each other and from concentration zones or bands containing the free enzyme and antibody components. In particular, the free enzyme component migrates faster and farther than the enzyme-antibody monoconjugate, which, in turn, migrates faster and farther than the enzyme-antibody polyconjugates as described above. Accordingly, the concentration zone containing the desired enzyme-antibody conjugate can then be removed to isolate the enzyme-antibody conjugate therefrom. For example, where an enzyme-antibody monoconjugate is desired, the zone adjacent to the zone containing the free enzyme component is removed and the monoconjugate isolated therefrom.

It is to be understood that depending upon the relative electrophoretic migration patterns of the enzyme-antibody conjugates and the free antibody component, the selected concentration zone or zones containing the desired enzyme-antibody conjugate may or may not contain free antibody component. Where such zone contains free antibody component, the free antibody component can be removed according to methods known in the art such as gel filtration, ion exchange, enzyme-affinity chromatography, and the like. Alternatively, the free antibody component present in the conjugate reaction mixture can be removed prior to application of the conjugate reaction mixture to the PAGE apparatus according to such aforementioned separation methods known in the art.

(iii) Isolation of Enzyme-Antibody Conjugates

According to the present invention, the enzyme-antibody conjugate (or conjugates) is normally isolated from the polyacrylamide gel by physically removing the concentration band containing the desired enzyme-antibody conjugate. The location of the band containing the desired enzyme-antibody conjugate, as well as the bands containing the free enzyme component, are determined with an enzyme activity stain which is applied to the face of the polyacrylamide gel in a horizontal position. The activity stain comprises a substrate for the particular enzyme component of the conjugate, and reacts with the enzyme to produce a detectable color which precipitates in place. Accordingly, the particular enzyme activity stain will depend upon the enzyme being employed as the enzyme component, and which can be selected by one skilled in the art. For example, where the enzyme component is $\beta$-D-galactosidase, a $\beta$-D-galactosidase activity stain such as 5-bromo-3-indoyl-$\beta$-D-galactoside coupled with 2-methoxy-4-morpholinobenzene-diazonium chloride can be employed.

Once the bands have been stained and resolved as heretofore described, one or more of the bands containing the desired enzyme-antibody conjugate is physically excised out of the gel slab and separately placed into the electroelution device. The electroelution device comprises an electrophoresis device which electrophoretically causes the enzyme-antibody conjugate to migrate out of the excised gel band into a chamber from which the isolated species is recovered.

The electroeluted enzyme-antibody conjugate is then assessed for purity by applying the isolated conjugate to an analytical PAGE apparatus which resolves any free enzyme component which may still be present into distinct concentration bands. The bands are visualized with an enzyme activity stain, and analyzed on a densitometer which quantitates the intensity of the individual bands, and the fraction of free enzyme or enzyme-antibody conjugates present determined therefore.

According to the method of the present invention, the enzyme-antibody conjugate preparations are isolated from their respective concentration bands and generally comprise greater than about 90% of the enzyme component present therein covalently coupled to an antibody component, usually greater than about 95%, more usually greater than about 99%. It is to be understood that the remaining 10%, 5% and 1% of the isolated preparations, respectively, are enzyme-antibody preparation contaminants comprising free enzyme components or undesired enzyme-antibody conjugates, depending upon the particular enzyme-antibody conjugate isolated and the proximate concentration bands adjacent thereto. For example, where a monoconjugate is desired, the predominant contaminant is the free enzyme component whereas where a diconjugate is desired, the predominant contaminant is a monoconjugate. In particular, it is possible to obtain purity levels as high as about 99.5%, where the enzyme-antibody conjugate comprises Fab' and $\beta$-D-galactosidase.

Immunometric Assay Method

The substantially pure preparation of the desired enzyme-antibody conjugate prepared according to the present invention is useful as a labeled reagent in immunoassays for determining the amount of analyte present in a liquid test sample. Generally, such immunoassays involve specific binding interactions between the analyte and a labeled reagent which form a specific binding reaction system comprising two species or forms of the labeled reagent, a bound species and a free species. The relative amount or proportion of the labeled reagent that results in the bound species compared to the free species is a function of the presence or amount of the analyte to be detected in the test sample.

For example, the enzyme-antibody monoconjugate of the present invention is especially useful in an immunometric assay involving the use of an immobilized form of the analyte or analog thereof. In particular, the test sample is contacted with the enzyme-antibody monoconjugate and the immobilized form of the analyte or analog thereof which are capable of binding with the antibody component of the monoconjugate. Accordingly, the amount of monoconjugate which becomes bound to the analyte in the test sample compared to that which becomes bound to the immobilized reagent is then determined and related to the amount of analyte present in the test sample.

Typically, the extent of binding is determined by employing an indicator compound which provides a detectable signal upon contact with the enzyme label of the monoconjugate of the bound or free species wherein the amount of enzyme detected and measured can be correlated to the amount of analyte present in a liquid test sample. Preferably, such indicator compound comprises a chromogenic enzyme substrate compound comprising a chromogen derivatized with an enzymatically cleavable group which, upon contact with the monoconjugate, is cleaved by the enzyme thereof to generate a detectable signal which can be measured with, for example, a reflectance photometer, and correlated to the amount of analyte present in the liquid test sample.

Reagent System

The present invention further provides a reagent system comprising all of the essential elements required to conduct a desired immunometric assay method as heretofore described. The reagent system is present in a commercially packaged form, as a composition or admixture where the compatability of the reagents will allow, in a test device configuration, or more usually as a test kit, i.e., a packaged combination of one or more containers, devices or the like holding the necessary reagents, and usually including written instructions for the performance of immunoassays.

Preferably, the reagent system will at least comprise (1) an immobilized form of the analyte as heretofore described and (2) a labeled reagent comprising a substantially pure enzyme-antibody conjugate preparation of the present invention, preferably a monoconjugate comprising one Fab' monovalent antibody fragment derived from a monoclonal antibody to the analyte under determination, coupled to one enzyme. Preferably, the reagent system will also include indicator means such as a test strip comprising a reagent pad incorporated with an indicator for the labeled reagent, preferably a chromogenic acridinone enzyme substrate as heretofore described.

In particular, the present invention will now be illustrated, but is not intended to be limited, by the following examples.

EXAMPLE 1

Preparation of Anti-Digoxin Monovalent Antibody Fragments (Fab') from Anti-Digoxin Divalent Antibody Fragments [F(ab')$_2$].

The monovalent antibody fragment (Fab') of an antidigoxin monoclonal antibody was prepared by pepsin digestion of the whole antibody to obtain the divalent antibody fragment [F(ab')$_2$] thereof which was reduced with mercaptoethylamine to obtain the desired monovalent antibody fragment (Fab') as follows:

(a) Preparation of Divalent Antibody Fragments [F(ab')$_2$]

A 1.0 M solution of sodium citrate (2.3 mL, pH 3.5) was added to 23.2 mL of freon-treated ascites fluid containing whole anti-digoxin monoclonal antibody and the pH adjusted to pH 3.5 with 1.0 N HCl. Pepsin (4.0 mL) was added (1.0 mg/mL) and the digestion of the whole antibody was carried out for 2 hours at 37° C with gentle stirring. The digestion reaction was stopped by adding 6.5 mL 1.0 M TRIS base to obtain the F(ab')$_2$ fragment. This material was divided into four aliquots and each was purified on a 17 mL ouabain affinity column (ouabain coupled to Sepharose® CL-6B, Pharmacia,Inc. Piscataway, N.J., USA), equilibrated with a PBS (0.1M sodium phosphate, 0.15M sodium chloride, pH 7.0)/0.02% NaN$_3$ buffer solution and the F(ab')$_2$ fragment which adsorbed to the ouabain in the column was eluted with 23 mM ouabain in PBS. The ouabain-eluted antibody was concentrated and dialyzed extensively by continuous flow against PBS/NaN$_3$ to obtain 62.3 mg of F(ab')$_2$ fragments.

(b) Alternate Method For Preparation of F(ab')$_2$ Fragments

Alternatively, F(ab')$_2$ fragments were prepared from IgG isolated from ascites fluid on a Bio-Rad MAPS® protein A column (Bio-Rad Laboratories, Richmond, Calif., USA) to obtain 7.7 mg IgG/mL ascites fluid. Pepsin was added to the purified IgG in 0.1 M sodium citrate (pH 3.5) at 1 mg/mL in a 1:33 weight ratio of pepsin to IgG, and the reaction was carried out at 37° C for 2 hours and the reaction stopped by adding 1.0 M TRIS base to bring the pH to approximately pH 7.0. The products were chromatographed on a 1.0×80.0 cm gel filtration column (AcA 22 Ultrogel, LKB, Sweden) in PBS/NaN$_3$ buffer to obtain a first peak containing the desired F(ab')$_2$ fragments and a second peak containing peptides and pepsin, and the purity of the F(ab')$_2$ fragments were assessed by SDS-polyacrylamide gel electrophoresis. The concentration of F(ab')$_2$ fragments were determined from the absorbance at 280 nm using an extinction coefficient of 1.48 (mg.cm/mL)$^{-1}$ and a molecular weight of 92,000 and the F(ab')$_2$ was stored at 4° C. in PBS/NaN$_3$ buffer.

(c) Reduction of F(ab')$_2$ Fragments to Fab' Fragments

The F(ab')$_2$ fragment solution (2.0 mL, 3.3 mg/mL) prepared according to method (a) of the present example was exchanged into 0.1 M sodium phosphate, 5.0 mM EDTA (ethylenediamine tetraacetic acid) buffer (pH 6.0) and 0.1 M mercaptoethylamine was added to a final concentration of 10.0 mM. The reduction reaction was carried out for 90 minutes at 37° C and the mercaptoethylamine was removed by dialysis against PBS with 5.0 mM EDTA in a stirred ultrafiltration cell (AMICON CORP., Danvers, Mass., USA). The concentration of Fab' fragments were 1.34 mg/mL, 6 mg (determined from the absorbance at 280 nm using an extinction coefficient of 1.48 (mg.cm/mL)$^{-1}$ and a molecular weight of 46,000). The sulfhydryl content of the Fab' fragments was measured with 4,4'-dithiopyridine [D. R. Grassetti & J. F. Murray, Jr., Arch. Biochem. Biophys., 119, 41(1967)] and was determined to be 3 sulfhydryls/-Fab'.

EXAMPLE 2

Preparation of Activated β-D-Galactosidase.

E. Coli β-D-galactosidase from the constitutive strain, A324–5 (obtained from I. Zabin, Dept. of Biological Chemistry, University of California at Los Angeles, Calif., USA) was stored as an (NH$_4$)$_2$SO$_4$ suspension with 0.02% NaN$_3$ at a concentration of 14 mg/mL. The β-D-galactosidase suspension (1.8 mL) was centrifuged to obtain a pellet which was dissolved in PBS to a volume of 2.1 mL (100% enzyme activity). The concentration was 11.8 mg/mL, 25 mg or 54 nmol (determined from the absorbance at 280 nm using an extinction coefficient of 2.43 (mg.cm/mL)$^{-1}$ and a molecular weight of 465,000). Any sulfhydryl groups on the β-D-galactosidase (typically less than or equal to 3 sulfhydryls) were alkylated in a reaction with a 20-fold molar excess of iodoacetamide for 30 minutes at room temperature in the dark. The reaction mixture was chromatographed on a 1.0×40.0 cm desalting column (BioGel® P-6DG, Bio-Rad Laboratories, Richmond, Calif., USA) in PBS buffer. The β-D-galactosidase peak was concentrated in a stirred ultrafiltration cell (AMICON) to 9.0 mg/mL (2.5 mL, 22.4 mg, 105% enzyme activity) and a 20-fold molar excess of succinimidyl-4-(N-maleimido-methyl)-cyclohexane-1-carboxylate (SMCC, Pierce Chemical Co., Rockford, Ill., USA) was added and the reaction carried out for 1.0 hour at room temperature with gentle stirring. The SMCC reaction mixture was desalted on a 1.0×40.0 cm desalting column (BioGel® P-6DG) in PBS containing 1.0 mM EDTA in a volume of 7.2 mL at 3.1 mg/mL (92% enzyme activity). The maleimide content of the activated β-D-galactosidase which eluted from the column was calculated from the difference between the sulfhydryl content (determined with 4,4'-dithiopyridine) of reduced glutathione in the absence and the presence of activated β-D-galactosidase, which was determined to be 5.4 maleimides/mole of β-D-galactosidase.

EXAMPLE 3

Preparation of Fab'-β-D-Galactosidase Conjugate.

Activated β-D-galactosidase (34.6 nmoles) in 5.2 mL PBS from Example 2 was combined with 104 nmoles of the Fab' fragment preparation from step (c) of Example 1 in 3.5 mL PBS, 5mM EDTA and the mixture was incubated with gentle stirring at 5° C for approximately 20 hours (99% enzyme activity). The resulting Fab'-β-D-galactosidase conjugate preparation was filtered through a 0.45 μ filter (97% enzyme activity) and exchanged into a 2-fold diluted preparative polyacrylamide gel electrophoresis (PAGE) buffer consisting of (undiluted) 89.0 mM TRIS base, 81.0 mM boric acid, and 2.5 mM EDTA adjusted to pH 8.6 with NaOH. The solution was concentrated to 0.8 mL (95% enzyme activity). Alternatively, the reaction mixture containing the Fab'-β-D-galactosidase conjugate preparation after incubation can be exchanged into PBS/NaN$_3$ buffer for storage prior to filtering.

EXAMPLE 4

Casting of Preparative Polyacrylamide Gel Electrophoresis Slab Apparatus.

A polyacrylamide gradient from 5%–8% of total monomer concentrations (% T) and 2% crosslinking (% C) was prepared employing the following materials:
(i) 40% T,2% C acrylamide in water;
(ii) 10X running buffer (1X=89.0 mM TRIS base, 82.0 mM boric acid, 2.5 mM EDTA, pH adjusted to 8.6 with NaOH);
(iii) 10% ammonium persulfate (w/v);
(iv) N,N,N',N'-tetramethylethylenediamine (TEMED).

Gel solutions (64.0 mL) of 5% T,2% C (8.0 mL 0% T, 2° C; 6.4 mL 10X running buffer; 49.6 mL water) and 8% T,2% C (12.8 mL 40% T,2% C; 6.4 mL 10X running buffer; 39.5 mL water; 9.6 g sucrose) were degassed for 1.0 hour, and 128 μL 10% ammonium persulfate and 20 μL of TEMED were added to each solution.

The 5%–8% T,2% C gradient employing the treated 5% T,2% C and 8% T,2% C gel solutions was made with a gradient maker (Pharmacia GM-1 Gradient Maker, (Pharmacia Inc., Piscataway, N.J., USA) and the gradient solution was pumped from the gradient maker with a peristaltic pump (Pharmacia P-3, 3.1 mm tubing, 4.5 setting, fast sprocket) into a slab gel mold apparatus (SE600, Hoefer Scientific Instruments, San Francisco, Calif., USA) with 6 mm spacers. The tubing outlet was fastened at the top of the glass plates in the center and the solution was permitted to run down the side of the glass and into the mold. After the gel was cast (approximately 45 minute pouring time), n-butanol was layered over the top of the gel and the gel was permitted to polymerize overnight at room temperature. A 10.5 cm sample well was made at the top of the vertical gel with a 10 mL 5%,2% acrylamide solution (1.25 mL 40% T,2% C; 1.0 mL 10X buffer; 7.75 mL water; 50 μL 10% ammonium persulfate; 20 μL TEMED) which was pipetted on either side of the spacer well to the top of the glass sandwich and permitted to polymerize at room temperature for 1 hour.

EXAMPLE 5

Purification of Fab'-β-D-Galactosidase Conjugate Preparation on Preparative Polyacrylamide Gel Electrophoresis Slab Apparatus.

(a) The Fab'-β-D-galactosidase conjugate preparation (0.34 mL) of Example 3 was diluted to 0.774 mL with 0.5X running buffer. To this was added 200 μL of bovine serum albumin-bromophenyl blue solution (20 mg/mL) and sucrose (5% w/v).

(b) The preparative polyacrylamide gel (from Example 4) and 5 liters of 1X running buffer were cooled to 4° C., and the Fab'-β-D-galactosidase conjugate preparation from step (a) of the present example was loaded to the sample well at the top of the vertical gel. The cooled 1X running buffer was recirculated between the upper and lower reservoirs of the electrophoresis slab apparatus with a peristaltic pump. The gel was electrophoresed at a constant voltage of 100 volts at 36 mA (initially) in a refrigerated room (4° C), and the electrophoresis was terminated 24 hours later at which point the amperage had dropped to 27 mA.

The electrophoresed gel was removed from the glass retainers of the electrophoresis slab apparatus and the resulting bands of protein were visualized with an enzyme activity stain consisting of 5-bromo-3-indoyl-β-D-galactoside coupled with 2-methoxy-4-morpholinobenzene-diazonium chloride, zinc chloride double salt in 0.3 M bicine and 10 mM MgCl$_2$ (pH 7.7).

EXAMPLE 6

Isolation of Fab'-β-D-Galactosidase Monoconjugate.

The protein band containing the desired Fab'-β-D-galactosidase monoconjugate of the stained, electrophoresed gel from Example 5 was excised with a knife and cut to a size of 1.0×11.0 cm. The excised monoconjugate gel band was placed into the cell of an electroelution device (Geluter ®, E-C Apparatus, St. Petersburg, Fla., USA) with a buffer of 50 mM HEPES (pH 7.4) and electrophoresed at a constant voltage of 100 volts at 6 mA to isolate the Fab'-β-D-galactosidase monoconjugate from the gel band.

The isolated monoconjugate was removed from the cell of the electroelution device, exchanged and concentrated in PBS/NaN$_3$, 1 mM MgCl$_2$, 0.4 mg/mL BSA to 1.32 mL. The recovery (based on enzyme activity) of monoconjugate from the reaction mixture loaded to the preparative PAGE apparatus was 17.2% (1.1 m9). The overall yield (synthesis and purification) of monoconjugate (based on enzyme activity) was 16.3%.

A final purification step of the monoconjugate was done on a gel filtration column (AcA 22 Ultrogel, LKB, Sweden) in order to remove residual Fab' fragments.

EXAMPLE 7

Characterization of Fab'-β-D-Galactosidase Monoconjugate Preparation.

The specific β-D-galactosidase and Fab' fragment activities of the isolated Fab'-β-D-galactosidase monoconjugate prepared as in Example 6 indicated that the ratio of Fab'-fragments (antigen binding sites) to β-D-galactosidase was unity on a molar basis, and equilibrium dialysis measurements (Hoefer Equilibrium Microvolume Dialyzer, Hoefer Scientific Instruments, San Francisco, Calif., USA) using tritiated digoxin indicated that the affinity constant for the Fab' fragment in the monoconjugate was essentially identical to the initial IgG affinity constant ($9 \times 10^{10}$ M$^{-1}$).

The Fab'-β-D-galactosidase monoconjugate preparation was further characterized on an analytical native PAGE apparatus. (Hoefer Vertical Slab Gel Unit SE600. Hoefer Scientific Instruments, San Francisco, Calif., USA). A 1.5 mm gradient gel (5–10% T,2% C) with tris-borate buffer (pH 8.6) was used. In this system, the free enzyme (β-D-galactosidase) band was completely separated from the monoconjugate band. The intensities of the visualized bands (enzyme activity stain, Example 5) were quantitated on a gel scanning densitometer (Model 620, Video Densitometer, Bio-Rad Laboratories, Richmond, Calif., USA). By this technique the contamination of free β-D-galactosidase in the monoconjugate band harvested from the preparative PAGE apparatus in Example 6 was determined to be 3%.

EXAMPLE 8

Immunoassay for the Determination of Digoxin.

The Fab'-β-D-galactosidase monoconjugate preparation of Example 6 was employed in an immunoassay for the determination of digoxin from a liquid test sample employing an immobilized form of digitoxigenin (a digoxin analog) as the immobilized reagent and an acridinone-β-D-galactopyranoside as the chromogenic enzyme substrate indicator compound.

(a) Immobilized Reagent

The immobilized form of digitoxigenin was prepared according to the method described in the copending U.S. patent application entitled "Substantially Stable Immobilized Hapten Reagent For Use In Immunometric Assays" (U.S. Ser. No. 939,902, filed Dec. 9, 1986), and incorporated by reference herein. According to such method, digitoxigenin in anhydrous pyridine was treated with 4-dimethylaminopyridine and p-nitrophenylchloroformate to obtain 3-digitoxigeninyl-p-nitrophenyl carbonate, which was then carboxy functionalized employing 6-aminocaproic acid and triethylamine in anhydrous pyridine to obtain 3-O-(5-carboxypentan-1-carbamoyl)digitoxigenin. The carboxy functionalized digitoxigenin in anhydrous N,N-dimethylformamide (DMF) was then treated with triethylamine, N-hydroxysuccinimide and N,N-dicyclohexylcarbodiimide to obtain 3-O-(5-carboxypentan-1-carbamoyl)-digitoxigenin (activated digitoxigenin).

The immobilized reagent comprising the activated digitoxigenin covalently bound to the external amine groups of an aminoethyl-derivatized polyacrylamide gel particle was prepared by first forming a suspension of 2.0 grams of Aminoethyl BIO-GEL® P-2 resin (Bio-Rad Lablratories, Richmond, Calif., USA; Lot No. 28945, 1.39 meq. amine functional groups/dry gram of resin) in 10 ml of DMF which was incubated at room temperature for 48 hours. A 0.01 ml aliquot of the supernate from the aminoethyl-derivatized BIO-GEL® P-2 resin in the DMF solution was removed and replaced with 0.01 ml of the activated digitoxigenin to form a reaction solution comprising 0.05 μmoles of activated digitoxigenin per dry gram of the resin and gently mixed on a rotary mixer (end-over-end agitation) at room temperature for 48. hours, washed with a buffer solution and water, and then dried by lyophylization.

(b) Chromogenic Enzyme Substrate Indicator Compound

The chromogenic indicator compound was prepared according to the method described in the copending U.S. patent application entitled "Chromogenic Acridinone Enzyme Substrates" (U.S. Ser. No. 939,855, filed Dec. 9, 1986), and incorporated by reference herein. According to such method, a 7-hydroxy-9,9-dimethyl-9H-acridin-2-one intermediate, is reacted with acetobromogalactose and silver oxide in ethylacetate/quinoline to prepare a 7-(tetra-O-acetyl-β-D-galactopyranosyloxy)-9,9-dimethyl-9H-acridinone, which is then hydrolyzed with sodium methoxide in methanol to obtain the desired 7-β-D-galactopyranosyloxy-9,9-dimethyl-9H-acridin-2-one indicator compound employed herein.

(c) Immunoassay

An immunoassay for the determination of digoxin employing the aforementioned reagents was performed as follows:

(i) a reaction mixture comprising 875 μL of a 0.30 nM solution of the monoconjugate and 35 μL of a serum test sample containing digoxin was incubated at room temperature for 6 minutes;

(ii) a reaction mixture comprising 780 μL of the reaction mixture of step (i) and 30 mg of lyophilized 0.05 μmoles digitoxigenin/gram resin was agitated for 4 minutes, and the resin was separated from the solution by a porous plastic filter; and (iii) a 30 μL aliquot was removed from the filtrate of the reaction mixture of step (ii) and applied to a reagent strip incorporated with acridinone-β-D-galactopyranoside.

The rate of color formation resulting from the interaction between the β-D-galactosidase and the acridinone-β-D-galactopyranoside was measured at 630 nm between about 60 to 80 seconds after sample application to the reagent pad, in order to determine the β-D-galactosidase activity of the monoconjugate labeled reagent from the filtrate, i.e., the bound species (Table 1). The reactivity measurements (Table 1) were made on a Seralyzer® reflectance photometer (Miles Laboratories, Inc., Elkhart, Ind., USA) attached to an HP-85 computer (Hewlett-Packard Company, Palo Alto, Calif., USA) through a multiple port interface. The resulting dose response to digoxin based upon the data shown in Table 1 is shown in FIG. 1.

TABLE 1

Dose Response to Digoxin

| Digoxin concentration ng/mL | Reactivity × $10^3$ |
| --- | --- |
| 0 | 1.01 |
| 0.6 | 1.71 |
| 1.2 | 2.31 |
| 2.4 | 3.59 |
| 3.6 | 4.79 |
| 5.0 | 6.28 |

EXAMPLE 9

Preparation of Anti-Thyroxine Monovalent Antibody Fragment (Fab') from Anti-Thyroxine Divalent Antibody Fragment (F[ab']$_2$).

The monovalent antibody fragment (Fab') of an anti-thyroxine monoclonal IgG antibody was prepared by preactivated papain digestion of the whole antibody to obtain the divalent antibody fragment F[ab']$_2$ thereof which was reduced with mercaptoethylamine to obtain the desired monovalent antibody fragment (Fab') as follows:

(a) Preparation of Divalent Antibody Fragment [F[ab']$_2$]

The F(ab')$_2$ fragment was prepared from anti-thyroxine IgG monoclonal antibody isolated from ascites fluid (Meloy Laboratories, Inc., Springfield, Va., USA, monoclonal antibody to T$_4$, 156/7) on a Bio-Rad MAPS® protein A column (Bio-Rad Laboratories, Richmond, Calif., USA) to obtain 14.5 mg IgG/mL ascites fluid. Papain [Sigma Chemical Co., St. Louis, Mo., USA, Type III, 2x crystallized from papaya latex in 0.05 M sodium acetate suspension, pH 4.5, preactivated by incubating with cysteine followed by gel filtration to obtain active enzyme according to the method described by Parham, et al., *J. Immunol. Methods*, Vol. 53, p. 133 (1982)] was added to the purified IgG (5.8 mL, 1.09 mg/mL) in 0.1 M sodium acetate, 3.0 mM EDTA (ethylenediamine tetraacetic acid), pH 5.5 at 0.62 mg/mL (1.02 mL) in a 1:10 weight ratio of papain to IgG. The digest was incubated for 40 minutes at 37° C., and the products were chromatographed on a 1.0×80.0 cm gel filtration column (AcA44 Ultrogel, LKB, Sweden) in PBS/NaN$_3$ buffer to obtain a first peak containing the desired F(ab')$_2$ and Fc antibody fragments and contaminating papain-associated digestion products, and a second peak containing bulk papain.

The first fraction from step (a) of the present example was treated with polyclonal anti-papain IgG (Cappel, Division of Cooper Diagnostics, Cochranville, Pa., USA, Lot No. 23655, Cat. No. 0100-1202) in order to complex and subsequently isolate any papain contamination from the desired F(ab')$_2$ antibody fragment. To the first gel filtration fraction (4.0 mL, 2.52 mg/mL, 2.0 mg of anti-papain IgG in PBS (1.08 mL, 1.85 mg/mL) was added and incubated overnight at 4° C. The solution was then chromatographed on a Bio-Rad MAPS ® protein A column which retained both the original Fc fragment from the digest and any anti-papain IgG which was complexed with the papain-associated digestion products. The purified F(ab')$_2$ fragment passed through the column in the application buffer. Analytical SDS-polyacrylamide gel electrophoresis indicated that the F(ab')$_2$ fragments purified in this way were free of papain contamination and of high purity. The concentration of F(ab')$_2$ fragments was determined to be 0.44 mg/mL (8.6 mL, 3.77 mg) from the absorbance at 280 nm using an extinction coefficient of 1.48 (mg cm/mL)$^{-1}$ and a molecular weight of 92,000. The F(ab')$_2$ fragments were stored at 4° C. as a solution in PBS/NaN$_3$ buffer.

(b) Reduction of F(ab')$_2$ fragments to Fab' fragments

The F(ab')$_2$ fragment solution (8.2 mL, 0.44 mg/mL) prepared according to step (b) of the present example was exchanged into 0.1 M sodium phosphate, 5.0 mM EDTA buffer (pH 6.0) to a concentration of 0.67 mg/mL (5.1 mL). Mercaptoethylamine was when added to a concentration of 10 mM and incubated for 60 minutes at 37° C. The reducing agent was removed by dialysis against PBS with 5.0 mM EDTA in a stirred ultrafiltration cell. The concentration of Fab' fragments (0.63 mg/mL, 5.3 mL) was determined from the absorbance at 280 nm using an extinction coefficient of 1.48 (cm[mg/mL])$^{-1}$ and a molecular weight of 46,000 daltons. The sulfhydryl group content of the Fab' fragments was measured with 4,4'-dithiopyridine [Grassetti, et al., *Arch. Biochem. Biophys.*, Vol. 119, p. 41 (1967)] and was determined to be 3 sulfhydryl groups per Fab' fragment.

EXAMPLE 10

Preparation of Anti-Thyroxine-β-D-Galactosidase Conjugate.

Activated β-D-galactosidase (23.6 nmoles in 3.5 mL PBS, prepared according to Example 2) was combined with 59.0 nmoles of anti-thyroxine Fab' fragments (prepared according to Example 1) in 4.3 mL PBS, 5 mM EDTA. The reaction solution was incubated for 20 hours at 5° C. The resulting Fab'-β-D-galactosidase conjugate preparation was filtered through a 0.1 μm filter and exchanged into two-fold diluted preparative polyacrylamide gel electrophoresis (PAGE) buffer consisting of (undiluted) 89.0 mM TRIS base, 81.0 mM boric acid, and 2.5 mM EDTA adjusted to pH 8.6 with NaOH. The conjugate solution was then concentrated to 1.1 mL in PAGE buffer.

EXAMPLE 11

Purification of Anti-Thyroxine Fab'-β-D-Galactosidase Conjugate Preparation on Preparative Polyacrylamide Gel Electrophoresis Slab Apparatus.

(a) The conjugate preparation (1.1 mL) prepared according to Example 10 (0.43 mL, 3.0 mg) was mixed with 50 mg sucrose and 200 μL of ovalbumin and 0.01% (v/v) bromophenyl blue.

(b) A preparative polyacrylamide gel was prepared according to Example 4 and the Fab'-β-D-galactosidase conjugate preparation solution from step (a) of the present example was electrophoresed as described in Example 5.

EXAMPLE 12

Isolation of Anti-Thyroxine Fab'-β-D-Galactosidase Monoconjugate.

The protein band containing the desired anti-thyroxine Fab'-β-D-galactosidase monoconjugate prepared according to Example 11 was excised and eluted as described in Example 6, with the exception that 1.0 mg of ovalbumin was added to the recovery well of the electroelution device.

The isolated monoconjugate was removed (17.0 mL) from the cell of the electroelution device, with rinses, and was exchanged and concentrated in PBS/NaN$_3$, 1.0 mM MgCl$_2$ to 2.25 mL. The recovery (based on enzyme activity) of monoconjugate from the reaction mixture loaded to the preparative PAGE apparatus was 13.2% (0.5 mg).

Additional purification of the monoconjugate was not necessary. In particular, the unreacted Fab' fragments from this particular clone remained at the top of the preparative PAGE gel and did not migrate so as to contaminate the monoconjugate band.

EXAMPLE 13

Characterization of Anti-Thyroxine Fab'-β-D-Galactosidase Monoconjugate Preparation.

The specific β-D-galactosidase and Fab' fragment activities (determined by RIA) of the isolated anti-thyroxine Fab'-β-D-galactosidase monoconjugate prepared according to Example 12 indicated that the ratio of Fab' fragments (antigen binding sites) to β-D-galactosidase (active tetrameric centers) was unity on a molar basis.

The anti-thyroxine Fab'-β-D-galactosidase monoconjugate preparation was further characterized by analytical native PAGE and quantitated as described in Example 7. The purity of this monoconjugate preparation was determined to be greater than 99.5%, and no free enzyme or other bands besides the monoconjugate band were observed on the gel.

What is claimed is:

1. A method for obtaining a substantially pure preparation of a conjugate comprising a single β-D-galactosidase molecule covalently coupled to a predetermined number of a monovalent antibody fragment selected from the group consisting of Fab and Fab', said method comprising the steps of:

(a) applying to a polyacrylamide gel electrophoretic support matrix a reaction mixture from the coupling of β-D-galactosidase with the monovalent antibody fragment, said reaction mixture comprising, as separately migratable species, at least free β-D-galactosidase and a population of β-D-galactosidase conjugates comprising one or more molecules of β-D-galactosidase covalently coupled to one or more of said monovalent antibody fragment;

(b) electrophoretically separating said free β-D-galactosidase and β-D-galactosidase conjugates into distinct concentration zones on said support matrix;

(c) staining the support matrix with a chromogenic β-D-galactosidase substrate to visualize bands containing the enzyme, (d) cutting and removing the gel band containing a desired β-D-galactosidase conjugate wherein greater than about 99% of β-D-galactosidase present in the preparation in such band is covalently coupled to the antibody fragment, and (e) eluting a substantially pure preparation of the desired β-D-galactosidase conjugate from the gel band removed in step (d).

2. The method of claim 1 further comprising the step of separating free monovalent antibody fragment from the desired β-D-galactosidase conjugate by gel filtration.

3. The method of claim 1 wherein the desired β-D-galactosidase conjugate is a monoconjugate having a single β-D-galactosidase molecule covalently coupled to a single Fab or Fab' fragment.

4. The method of claim 1 wherein the desired β-D-galactosidase conjugate has a single β-D-galactosidase molecule covalently coupled to two or more predetermined number of Fab or Fab' fragments.

5. The method of claim 1 wherein said monovalent antibody fragment is Fab'.

* * * * *